United States Patent [19]

Thoma et al.

[11] Patent Number: 4,965,698
[45] Date of Patent: Oct. 23, 1990

[54] CAPACITANCE HUMIDITY SENSOR

[75] Inventors: Paul E. Thoma, Wauwatosa; Jeannine O. Colla, Mequon, both of Wis.

[73] Assignee: Johnson Service Company, Milwaukee, Wis.

[21] Appl. No.: 414,129

[22] Filed: Sep. 27, 1989

[51] Int. Cl.$^5$ .................. H01G 7/00; H01G 5/20; G01N 27/12
[52] U.S. Cl. .................. 361/286; 29/25.42; 73/336.5
[58] Field of Search .................. 29/25.42; 338/35; 361/323, 286; 73/336.5

[56] References Cited

U.S. PATENT DOCUMENTS

| | | | |
|---|---|---|---|
| 3,458,845 | 7/1969 | Thoma | 338/35 |
| 3,547,897 | 12/1970 | Patton | 260/77.5 |
| 3,582,728 | 6/1971 | Thoma | 73/336.5 X |
| 3,590,347 | 6/1971 | Gottlob et al. | 361/323 X |
| 3,802,268 | 4/1974 | Thoma | 73/336.5 |
| 3,939,116 | 2/1976 | Johnson | 260/47 CB |
| 4,105,616 | 8/1978 | Patton | 521/62 |
| 4,164,868 | 8/1979 | Suntola | 73/336.5 |
| 4,298,855 | 11/1981 | Mills | 338/35 |
| 4,305,112 | 12/1981 | Heywang et al. | 361/286 |
| 4,332,976 | 6/1982 | Hawkins | 174/107 |
| 4,337,658 | 7/1982 | Motchenbacher et al. | 73/336.5 |
| 4,345,301 | 8/1982 | Nelson | 361/286 |
| 4,438,480 | 3/1984 | Chambaz et al. | 361/278 |
| 4,500,940 | 2/1985 | Kuisma et al. | 361/286 |
| 4,558,393 | 12/1985 | Tanaka et al. | 361/286 |
| 4,564,882 | 1/1986 | Baxter et al. | 361/286 |
| 4,603,372 | 7/1986 | Abadie et al. | 361/286 |
| 4,761,710 | 8/1988 | Chen | 361/286 |
| 4,793,182 | 12/1988 | Djorup | 73/336.5 |

OTHER PUBLICATIONS

Thoma, *IEEE Transactions on Components, Hybrids, and Manufacturing Technology*, vol. CHMT-2, No. 3, 1979, pp. 321-323.
Henderson et al., *Poly(parabanic) Acids-A New Family of Thermoplastics* pp. 669-674.
Patton, *Polymer Preprints*, vol. 12, No. 1, Mar. 1971, pp. 162-169.

*Primary Examiner*—Donald A. Griffin
*Attorney, Agent, or Firm*—Foley & Lardner

[57] ABSTRACT

A capacitance humidity sensor according to the invention has a dielectric film core which is in contact with a pair of polymeric conductive layers bonded to opposite faces of the core. The dielectric core is made of a polymeric material having a dielectric constant which varies substantially linearly with humidity, such as a polyimide or polyparabanic acid. The conductive layers are made of a polymeric material having conductive particles, such as carbon particles, dispersed therein. Such conductive layers provide superior performance and corrosion resistance in comparison to the metal films commonly employed in the prior art.

47 Claims, 4 Drawing Sheets

CAPACITANCE HUMIDITY SENSOR

TECHNICAL FIELD

This invention relates to capacitance humidity sensors, particularly to humidity sensors having a moisture sensitive dielectric layer interposed between a pair of conductors.

BACKGROUND OF THE INVENTION

One type of known humidity sensor comprises a capacitor having a dielectric constant which changes as a function of humidity. Such capacitance humidity sensors have been in the form of a dielectric layer composed of a polymer such as polyimide and a thin metal electrode conducting layer, often made of gold. See Chen U.S. Pat. No. 4,761,710 issued Aug. 2, 1988, Abadie et al. U.S. Pat. No. 4,603,372 issued July 29, 1986, Kuisma et al. U.S. Pat. No. 4,500,940 issued Feb. 19, 1985, Chambaz et al. U.S. Pat. No. 4,438,480 issued Mar. 20, 1984, Heywang et al. U.S. Pat. No. 4,305,112 issued Dec. 8, 1981, Nelson U.S. Pat. No. 4,345,301, issued Aug. 17, 1982, Mills U.S. Pat. No. 4,337,658, issued July 6, 1982, and Suntola U.S. Pat. No. 4,164,868 issued Aug. 21, 1979. If such devices are to function well, at least one electrode must be permeable to water, have a low electrical resistance, and be relatively insensitive to corrosion. When an ultra thin gold electrode is used, good electrical conductivity and good permeability can be achieved. However, such capacitors have poor corrosion resistance. The thin gold electrode can be rapidly destroyed by sulfur-based pollutants or chlorine in the air surrounding a swimming pool.

Polyimide is a particularly useful dielectric for such sensors because its dielectric constant is linearly proportional to its moisture content. Furthermore, the excellent thermal resistance of polyimide makes it useful in capacitance humidity sensing devices. However, the bonding between the polyimide and metal electrode layers is difficult to obtain without the use of adhesives because of the dissimilarity between the metal and plastic.

Conductive compositions comprising conductive particles, such as particles of silver or carbon black, dispersed in resins such as polyimide, are generally known. See, for example, Takenaka U.S. Pat. No. 3,697,450, issued Oct. 10, 1972, describing resistance films. Other known humidity sensors have employed successive layers of cross-linked polymeric resin materials such as cellulose acetate butyrate cross-linked with urea formaldehyde resin. In one such sensor, a cross-linked cellulose acetate butyrate core containing conductive particles such as carbon is sandwiched between a pair of outer resin layers free of carbon particles. See Thoma U.S. Pat. No. 3,458,845, issued July 29, 1969. In other capacitive humidity sensors, the outer resin layers contain the conductive particles, and the inner resin layer does not; see Thoma U.S. Pat. Nos. 3,582,728, issued June 1, 1971, 3,802,268, issued Apr. 9, 1974, and *IEEE Transactions on Components, Hybrids, and Manufacturing Technology*, Vol. CHMT-2, No. 3, 1979, pages 321-323. Baxter et al. U.S. Pat. No. 4,564,882, issued Jan. 14, 1986, describes a humidity sensing element wherein the dielectric layer can be made from either cellulose acetate butyrate or polyimide.

Polyparabanic acids are known polymers used in a variety of applications. These polymers are generally defined as:

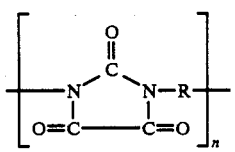

wherein R is an organic moiety which may be aromatic, aliphatic or alicyclic. See Henderson et al., "Poly(parabanic) Acids-A New Family of Thermoplastics" pp. 660-674. Poly(iminoimidazolidinediones) and other heterocyclic polymers related to PBA in structure are also known, and have been used to make films. See, for example, Patton U.S. Pat. Nos. 3,547,897, issued Dec. 15, 1970 and 4,105,616, issued Aug. 8, 1978, Johnson et al. U.S. Pat. No. 3,939,116, issued Feb. 17, 1976, and *Polymer Preprints*, Vol. 12, No. 1, Mar. 1971, pp. 162-169. Hawkins U.S. Pat. No. 4,332,976, issued June 1, 1982, describes PBA tape used in coaxial cables.

Screen printing has been suggested as a method for forming certain types of layers in humidity sensors. Mills U.S. Pat. No. 4,298,855, issued Nov. 3, 1981, which describes forming electrical resistors comprising carbon particles dispersed in a polymer film by such a process. Djorup U.S. Pat. No. 4,793,182, issued Dec. 27, 1988, describes a constant temperature hygrometer wherein resistive conductors are formed by silk screen printing.

The present invention addresses the various drawbacks with known capacitance humidity sensors discussed above, and provides a humidity sensor having a number of unexpected superior characteristics.

SUMMARY OF THE INVENTION

A capacitance humidity sensor according to the invention has a dielectric core which is in contact with a pair of conductors. According to a preferred aspect of the invention, a pair of conductive layers are bonded to opposite faces of the core. The dielectric core is made of a plastic material having a dielectric constant which varies substantially linearly with humidity, and the conductive layers are made of a plastic material having conductive particles dispersed therein. Such conductive layers provide superior performance and corrosion resistance in comparison to the metal films commonly employed in the prior art.

According to a further aspect of the invention, a method for making a humidity sensor element involves applying liquid compositions containing a substantially electrically non-conductive polymer, conductive particles and a carrier liquid to opposite sides of the dielectric film. Such a method is conveniently carried out by screen printing directly on both sides of the film.

DETAILED DESCRIPTION

Figure 1:
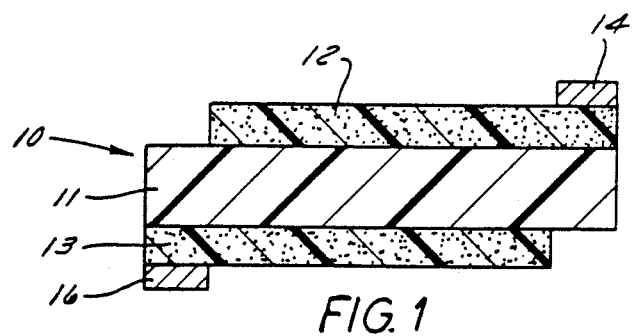
FIG. 1 a cross-sectional view of a humidity sensing film element according to the invention.

The present invention can provide a capacitance humidity sensor element in the form of a thin, flexible film. Referring to FIG. 1, a humidity sensor element 10 according to the invention includes a dielectric film 11 having a pair of electrically conductive layers 12, 13 on opposite sides thereof. Silver contacts 14, 16 on layers 12, 13 connect the sensor element to a source of electrical current. According to one aspect of the invention, the specific plastics which film 11 and layers 12, 13 are made of give the sensor element 10 advantageous properties in a manner not achieved in the prior art.

Dielectric film 11 is a water absorbing material having a dielectric constant which changes predictably (preferably essentially linearly) as a function of relative humidity. A specific class of polymers useful as the dielectric layer of the humidity sensor of the invention each have backbone chains containing heterocyclic units in which one or more atoms in the heterocyclic unit is nitrogen, one or more carbon atoms in the heterocyclic unit has an oxygen atom double bonded to it (i.e. the unit contains one or more keto groups) and the heterocyclic unit is bonded into the polymer backbone through one or more nitrogen atoms of the heterocyclic ring.

Film 11 is preferably made of a plastic of the general formula:

wherein A is a unit containing a heterocyclic unit including at least one —N—C=O linkage therein, B is an aromatic, alicyclic, or aliphatic, substituted or unsubstituted hydrocarbon unit, such as a substituted or unsubstituted alkylene, arylene, or aralkylene group, and n is greater than about 10, preferably greater than about 1000, wherein both A and B are substantially free of hydroxyl (—OH) groups. The value of n, i.e., the molecular weight of the polymer, is not critical so long as the chains are sufficiently long to form a flexible film. The cellulose acetate butyrate dielectric layers employed in the prior art have —OH groups which may contribute to the long term deterioration of the sensor, and thus the polymer dielectric core of the present invention should be essentially free of hydroxyl groups.

Figure 3:
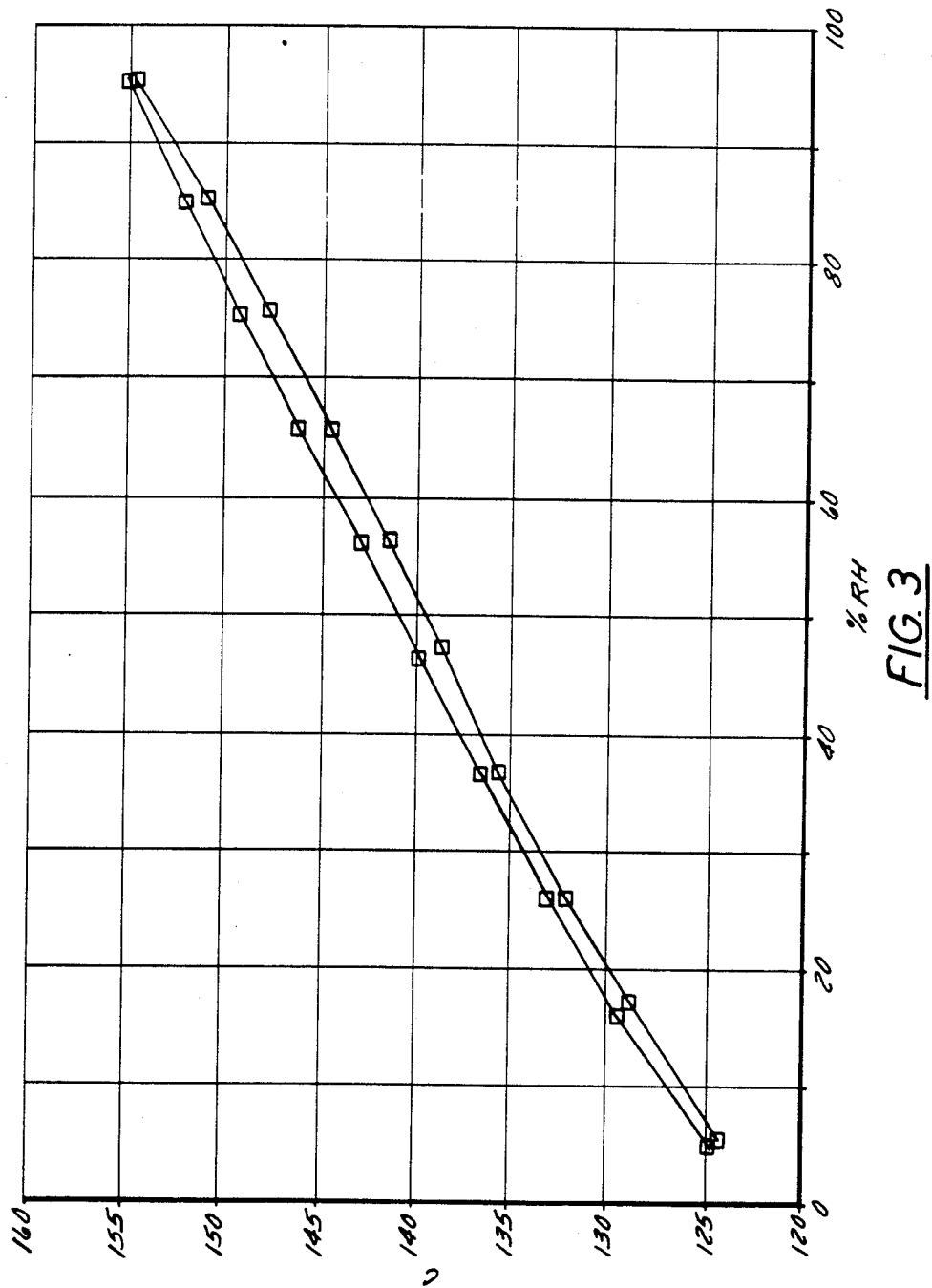
FIG. 3 is a graph plotting relative humidity versus capacitance in picofarads for a humidity sensor according to the invention.

Polymers of the foregoing formula are particularly useful as dielectric film materials because the hysteresis curves for such plastics are substantially linear under a broad range of conditions (see FIG. 3). The resulting change in capacitance for a given change in humidity is remarkably constant over a temperature range of about 15° to 50° C. (see FIG. 4), allowing the humidity sensor to be employed even in extreme conditions.

As unit A, groups having one or more phthalimide or imidazolidinetrione ring structures of the formula:

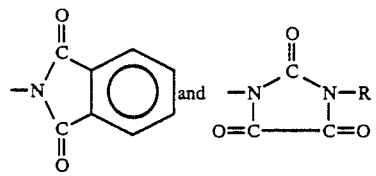

are preferred. Such groups include, for example:

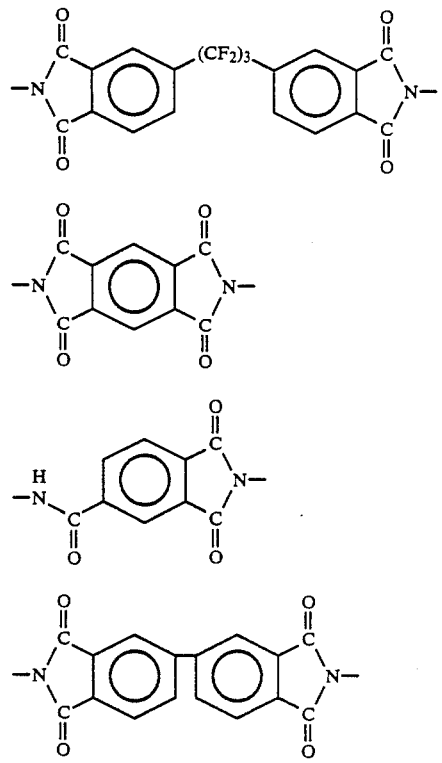

As unit B, groups of the formula:

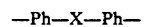

are preferred, wherein Ph is a phenylene group and X is an oxygen atom or a lower alkylene group, especially —CH2—.

Specific polymers useful as the dielectric film include polyimides, poly(amide-imides), poly(parabanic acid), poly(iminoimidazolidinediones), and the like. Polymers made of units of the specific formulas:

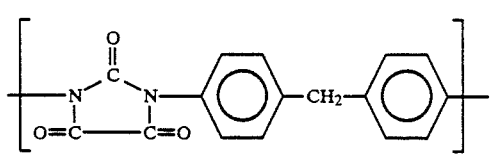

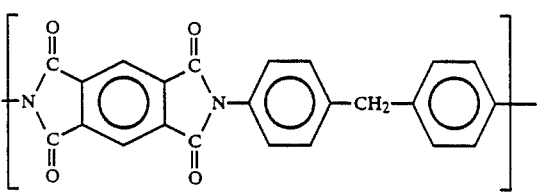

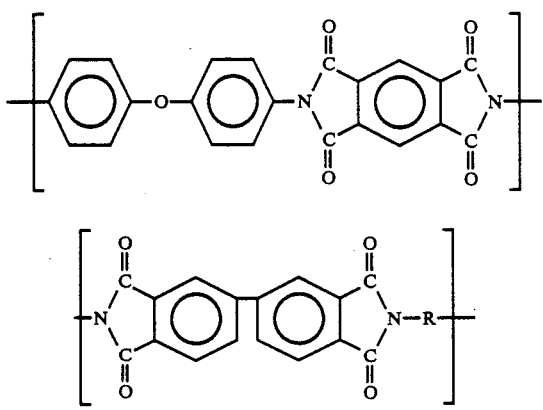

are especially preferred.

The conductive layers 12, 13 consist of a polymer matrix with conductive particles suspended within the polymer matrix. In conductive layers 12, 13, a wide variety of polymers can be employed. The polymers should be moisture pervious, i.e. should transmit humidity through to the dielectric layer, should bond securely to the dielectric film, and can be crosslinked for greater strength and durability. For these purposes, in a preferred embodiment, the polymeric matrix of the conductive layers is the same as the polymer used in the dielectric layer, since this assures maximum bonding affinity between the conductive layers and the dielectric.

Certain crosslinked polymers are also useful. Such crosslinked polymers can be formed by the reaction of a compound containing glucoside chains, such as a cellulosic material, and a monomer or partial polymer capable of reacting with the hydroxyl groups of the glucosides. The glucoside-containing compound can be cellulose or a cellulose ester in which the esterifying acids contain up to 20 carbon atoms and preferably up to six carbon atoms. Specific examples are cellulose nitrate, cellulose triacetate, cellulose butyrate, cellulose propionate, cellulose succinate, cellulose phthalate, or the like. Mixed cellulose esters such as cellulose acetate-butyrate, cellulose acetate-propionate, cellulose ethers in which the etherifying alcohol contains up to eight carbon atoms, such as ethyl cellulose, methyl cellulose, hydroxypropylmethyl cellulose, and hydroxybutylmethyl cellulose can also be employed. The stabilizing monomer or partial polymer can take the form of urea-formaldehyde, phenolformaldehyde, melamine-formaldehyde, triazineformaldehyde, hexamethoxymethylmelamine, glyoxal, 2-hydroxyadipaldehyde, and the like.

To achieve an integral bond between the conductive layers and the dielectric core, physical and/or chemical bonds must exist between the layers. For this purpose, polymers of cellulose acetate butyrate crosslinked with urea-formaldehyde or melamine-formaldehyde have proven highly effective as the polymeric matrix for the conductive layers. These polymers have been found to have similar thermal expansion coefficients as the heterocyclic polymers used in the dielectric layer, and thus resist delamination during use due to changing temperatures.

It has also been found that uncrosslinked polymers such as cellulose acetate butyrate can be bonded to a polyimide dielectric core by applying the cellulose acetate butyrate to the core layer as a solvent solution, and then heating the dried cellulose acetate butyrate on the polyimide or other core plastic to at least about 177° C. for several (e.g., 15) minutes to form a strong adhesive bond between the cellulose acetate butyrate and the polyimide core.

The conductive particles used in the present invention render layers 12, 13 conductive. Layers 12, 13 should each have a resistivity of 500,000 ohm-cm or less, preferably 125,000 ohm-cm or less, as compared to dielectric film 11, which generally has a resistivity of at least about $10^{13}$ ohm-cm, preferably at least about $10^{15}$ ohm-cm at 25° and 50% relative humidity. Preferred conductive particles include particles of carbon, particularly long chaining-type carbon which may be oxidized, deoxidized, or graphitized, carbides of tungsten, zirconium, tantalum, niobium, and titanium, metal oxides such as $ReO_3$, $TiO$, $NbO$, $MoO_2$, $RuO_2$, $SrVO_3$, $LaNiO_3$, $TiO_2$ doped with pentavalent niobium, and combinations thereof. The particle size of the conductive particles is not critical, but particles having an average particle size (diameter) of 10 microns or less, especially 1 micron, or less, are preferred. The conductive particles are generally used in an amount in the range of about 10 to 80 percent by weight, the balance being the polymeric matrix (20–90 wt.%).

Chain-forming carbon particles are most preferred for use in the invention because these particles form conductive bridges through the polymeric matrix. The electrical conductivity of the carbon particles is further enhanced by heating the particles to a temperature sufficient to deoxidize the particles. This is done, for example, by heating the particles to 1093° C. (2000° F.) for 1 hour under vacuum. It is not essential that the carbon be deoxidized. Carbon pellets, such as Vulcan XC-72 made by the Cabot Corporation, are most preferred.

Conductive layers 12, 13 have a molecular structure which allows a high level of water transmission, whereby water molecules from the air transfer rapidly through the conducting layer to the dielectric layer. This ensures that the humidity sensor response time will be short.

The thickness of layers 12, 13 also influences the response time of the sensor to changes in humidity. Layers 12, 13 should have a thickness of 0.01 inch or less, particularly 0.001 inch or less, to allow sufficiently rapid response time, e.g., 15 minutes or less. The dielectric film may be made as thin as possible for the desired capacitance and film strength, and, unlike many known sensors, can be thinner by half or more than the conductive layers. Film 11 can, for example, have a thickness of 0.005 inch or less, especially 0.0005 inch or less.

The resulting element 10 is extremely light and thin, and represents a departure from many prior sensors employing a rigid base. According to the method of the invention described in detail below, a film comprising the dielectric layer is made prior to the formation of the outer, integrally bonded conducting layers. Since the dielectric core is prepared as a separate film, its thickness, electrical properties, and composition can be closely controlled.

Figure 2:
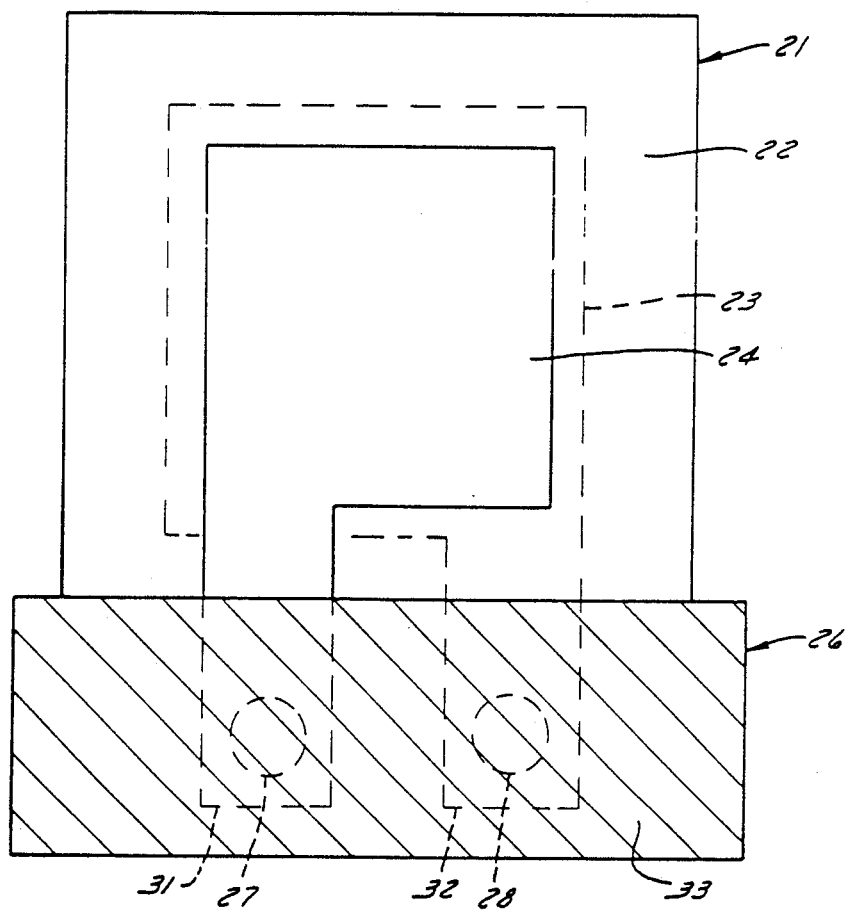
FIG. 2 is a top view of a humidity sensor according to the invention.

FIG. 2 illustrates a humidity sensor 21 according to the invention. Sensor 21 includes a dielectric film 22 made of a polymeric material as described above, a pair of conductive layers 23, 24 formed on opposite sides of film 22, and a holder 26. Outer conductive layers 23, 24 form the plates of the capacitor. Layers 23, 24 cover selected areas on opposite sides of dielectric film 22. The overlapping areas of the conductive layers 23, 24 comprise the active portion of the capacitance humidity sensor. Spots 27, 28 of conductive material, such as silver paint, are applied over conducting layers 23, 24 in areas where the layers 23, 24 do not overlap, for example, in elongated tab portions 31, 32 which extend into holder 26. Electrical contact is made to spots 27, 28 by means of one or more conductive metal plates 33 forming part of holder 26 used to mount the humidity sensor.

Humidity sensing element 21 may be used in combination with a variety of conventional circuitry to provide a humidity sensor. See, for example, the circuits described in Thoma U.S. Pat. Nos. 3,582,728, and 3,802,268, and Carusillo U.S. Pat. Nos. 4,558,274 and 4,661,768, the entire contents of which are hereby incorporated by reference herein. Such a system will generally include the humidity sensing element 21, a humidity indicator, such as a meter, an electrical power source, and circuitry for interconnecting the sensor element, power source, and indicator. The indicator provides a visual indication of changes in relative humidity as related to dielectric constant changes in the dielectric film. The indicator can be replaced by a control element if the sensor will be used to control the operation of a device such as a humidifier, air conditioner or dehumidifier.

The humidity sensor element of the invention can be made by forming the conductive layers directly on a piece of the dielectric film. First, a liquid composition containing the electrically non-conductive polymer, conductive particles and a carrier liquid, such as a solvent for the polymer, is applied to a piece of the thin, flexible dielectric film. If the conductive layers are to have a particular shape, the composition is selectively applied to a predetermined area on one face of the film. Then, the composition is dried under conditions effective to form a water-permeable conductive layer integrally bonded to the film. The conductive layer is made of the non-conductive polymer having the electrically conductive particles distributed therein which make the layer conductive.

After the first liquid composition has been dried and, if needed, cured to crosslink the polymer, a second liquid composition containing an electrically non-conductive polymer, electrically conductive particles and a carrier liquid is applied to the other side of said film. This second composition is generally identical to the first one, so that the resulting conductive layers will be as uniform as possible. The second composition is dried under conditions effective to form a water-permeable, second conductive layer integrally bonded to the film opposite the first conductive layer.

Screen printing is a particularly useful method for applying the liquid compositions to the film, as described in Example 1 below. The dielectric film, which is very thin and flexible, can be held in place by suction applied through a fine screen holder positioned beneath the film. A suitable stencil is placed over the film, and then the film is screen printed using a conventional thick film screen printer. The film is then removed from the printer and dried, e.g. by placing it in an oven, to remove the solvent and, if a cross-linkable polymer is being used, to cure the polymer. For the latter purpose the liquid conductive composition may contain a small amount of crosslinking catalyst together with a catalyst stabilizer which prevents the polymer from cross-linking until the drying step.

The foregoing procedure can then be repeated by inverting the film on the screen printer and printing a second conductive layer on the other side of the film opposite the first layer. The second layer overlaps the first layer in the manner shown in FIG. 2, and the area of overlap defines the capacitor. The second layer is then dried and cured in the same manner as the first layer. This process provides a humidity sensor element easily and inexpensively using conventional equipment. The foregoing process can further be used to make any type of thin humidity sensor element having the structure shown in FIG. 2, and is not limited to elements wherein the dielectric is a polyimide, polyparabanic acid, or the like.

The humidity sensing element of the invention provides a number of advantages not achieved by comparable elements in the prior art. A humidity sensing element having cellulose acetate butyrate as the dielectric layer and carbon-filled cellulose acetate butyrate as the conductive layers suffers from long term deterioration due to the presence of —OH groups within the dielectric polymer. A humidity sensing element utilizing metal conductive layers and a polyimide core, on the other hand, suffers from corrosion of the metal layers in corrosive environments and often suffers from separation of the conductive layers due to the poor affinity of the metal for the underlying plastic. In particular, differences in expansion coefficient of the metal and plastic can cause the layers to become separated after being subjected to substantial temperature changes over a period of time.

The invention addresses these disadvantages by combining a deterioration-resistant dielectric layer with corrosion resistant conductive layers. As the example below demonstrates, such an element can provide accurate humidity readings even in air containing chlorine, as commonly employed in indoor swimming pools. The conductive layers of the invention, particularly when crosslinked, are highly resistant to many forms of chemical corrosion and are thus suitable for environments such as hospitals in which chemicals (such as strong disinfectants) permeate the air. Further, since the element of the invention is a flexible film having thin conductive layers, it provides rapid response times with changes in relative humidity. The film element of the invention is also simple, small, and inexpensive in comparison to many conventional sensor elements.

A further, unexpected advantage of the humidity sensing element of the invention is that it can provide accurate humidity measurements at relative humidities of 90% and higher. Most conventional humidity sensors are not accurate at such levels, i.e. can deteriorate to the point of providing widely variable "banana"-shaped hysteresis curves.

A further advantage of the invention lies in the use of polyparabanic acid as the dielectric in a capacitance humidity sensor. Both polyparabanic acids and polyimides provide hysteresis curves which are close to linear, resulting in accurate, reproducible humidity measurements.

The foregoing description, and the examples below, are of preferred forms of the invention, and the invention is not limited to the specific forms shown. Modifications may be made in the design and composition of the invention without departing from the scope of the invention as expressed in the appended claims. Several embodiments of the invention are illustrated in the following examples:

EXAMPLE 1

The following procedure was used to fabricate a film-type capacitance humidity sensor. The dielectric polymer in this example is Kapton ® polyimide and the conductive humidity transmitting layers were composed of cellulose acetate butyrate ester and conductive deoxidized carbon.

The following procedure was used to prepare a liquid formulation of the materials used to form the conductive layers of a sensor according to the invention. The formulation had the following chemical composition, by weight:

- 42.5% Methyl ethyl ketone (solvent)
- 37.2% Butyrophenone (solvent)
- 1.6% Tripropylamine (catalyst stabilizer)
- 9.3% Beckamine 21-511 (Urea-formaldehyde resin, 60% urea-formaldehyde, 40% nbutyl alcohol)
- 5.2% Cellulose acetate butyrate (EAB-381-20)
- 2.3% Deoxidized Vulcan XC-72 carbon pellets The above composition was mixed together on a ball mill for seven days. This turns the carbon pellets into smaller particles which become dispersed in the liquid to create a liquid-solid suspension. The mixture is then vacuum evaporated to a viscosity of 14,000 to 18,000 cps on a Brookfield Synchro-lectric Viscometer. A well-mixed solution is prepared containing an additional 1.6% tripropylamine and 0.3% 50/50 p-toluenesulfonic acid/n-butyl alcohol mixture based on the initial weight of the conductive layer solution. These ingredients are added to the vacuum-evaporated composition and the resulting composition is mixed on a ball mill for at least about 16 hours. The conductive composition is then ready for application to a dielectric film.

To prepare the first conductive layer, a 325 mesh stainless steel screen with a 0.5 mil imaged photo emulsion is placed on a thick film screen printer (C. W. Price Model 8010). A porous stainless steel workpiece holder is mounted on the vacuum hold-down plate of the printer. The holder has a fine porosity, for example 325 mesh, which is desirable to facilitate vacuum hold-down of the dielectric film. A 2"×2" square of 0.3 mil Kapton ® polyimide film is centered on the stainless steel mesh holder beneath the screen with imaged photo emulsion. An optical registration system on the printer is used to position the polyimide film. Printing parameters such as squeegee pressure and screen snap off distance are adjusted and set for precision deposition of the conductive layer formulation. A small amount of the conductive layer formulation, in the form of a flowable liquid, is applied by hand to the imaged stainless steel screen. The printer is then cycled to automatically print the configuration for the first conductive layer onto the polyimide dielectric film.

To maintain the film surface in a uniform, horizontal position during the elevated temperature cure, another porous stainless steel vacuum hold-down fixture is used. The polyimide film having the first conductive layer printed thereon is dried, placed onto the vacuum hold-down fixture, and heated to 177° C. for 15 minutes to ensure that the conductive formulation is crosslinked and bonded to and polyimide film. The screen used to make the first conductive layer is removed and replaced on the thick film screen printer by another 325 mesh stainless steel screen with 0.5 mil imaged photo emulsion. The polyimide film with the first conducting layer is turned over and placed onto the stainless steel mesh vacuum hold-down fixture. The second conducting layer is printed onto the reverse surface of the polyimide dielectric film in the same manner as the first conducting layer was printed. The polyimide film having the second conducting layer is placed onto the vacuum hold-down fixture, dried, and heated at 177° C. for 15 minutes.

A conductive silver ink is dispensed by pen, brush, or screen printer onto the screen printed films in designated areas to serve as electrical contacts. The 2" by 2" polyimide film is then cut into individual sensor elements, and the finished film-type capacitance humidity sensors are inserted into protective holders having electrical connectors.

Automatic thick-film screen printing was used in this example because its precision lends itself to the manufacture of sensors according to the invention. Other techniques have also been used with acceptable results, for example, a graphic arts paintbrush was used to apply conductive humidity transmitting formulations to the surface of the humidity sensitive dielectric film. An air brush is also suitable for depositing conductive layers onto the surfaces of a dielectric film.

EXAMPLE 2

The following composition is prepared in the same manner as in Example 1 to form a conductive electrode formulation:

- 79.7% Diacetone alcohol (solvent)
- 1.6% Tripropylamine (catalyst stabilizer)
- 9.3% Beckamine 21-511
- 5.2% Cellulose Acetate Butyrate (EAB-381-20)
- 2.3% Vulcan XC-72 carbon pellets (graphitized)

The resulting formulation was used to make the conductive layers of a humidity sensor element in the same manner as described in Example 1, including the steps of vacuum evaporation and addition of further tripropylamine and 50/50 p-toluenesulfonic acid/n-butyl alcohol mixture.

EXAMPLE 3

The following procedure was used to determine the humidity sensing characteristics of the capacitance humidity sensor of the invention. The sensor element prepared in Example 1 is placed in a test fixture inside a Shinyei Humidity Cabinet. The temperature within the cabinet is held constant at 25° C. while the humidity is set at 5% RH. The relative humidity is determined by measuring the dew point and temperature of the air inside the cabinet using a General Eastern Dew Point Hygrometer and then calculating the percent RH.

The humidity sensor was allowed to stabilize at the selected % RH for one hour and then a capacitance reading was taken. The humidity in the cabinet was increased by steps of 10% RH until a maximum humidity of 95% RH was reached. Capacitance readings are taken at each step. The humidity was then decreased by 10% RH and capacitance readings are taken until a value of 5% RH was reached. At each step, the humidity sensor was allowed to stabilize for one hour before a capacitance reading was taken. The temperature was held constant throughout.

A hysteresis curve of capacitance versus percent relative humidity was plotted using the data obtained. The resulting narrow, linear hysteresis curve, as set forth in FIG. 3, demonstrates that the sensor of the invention is a properly functioning capacitance-type humidity sensor.

EXAMPLE 4

Figure 4:
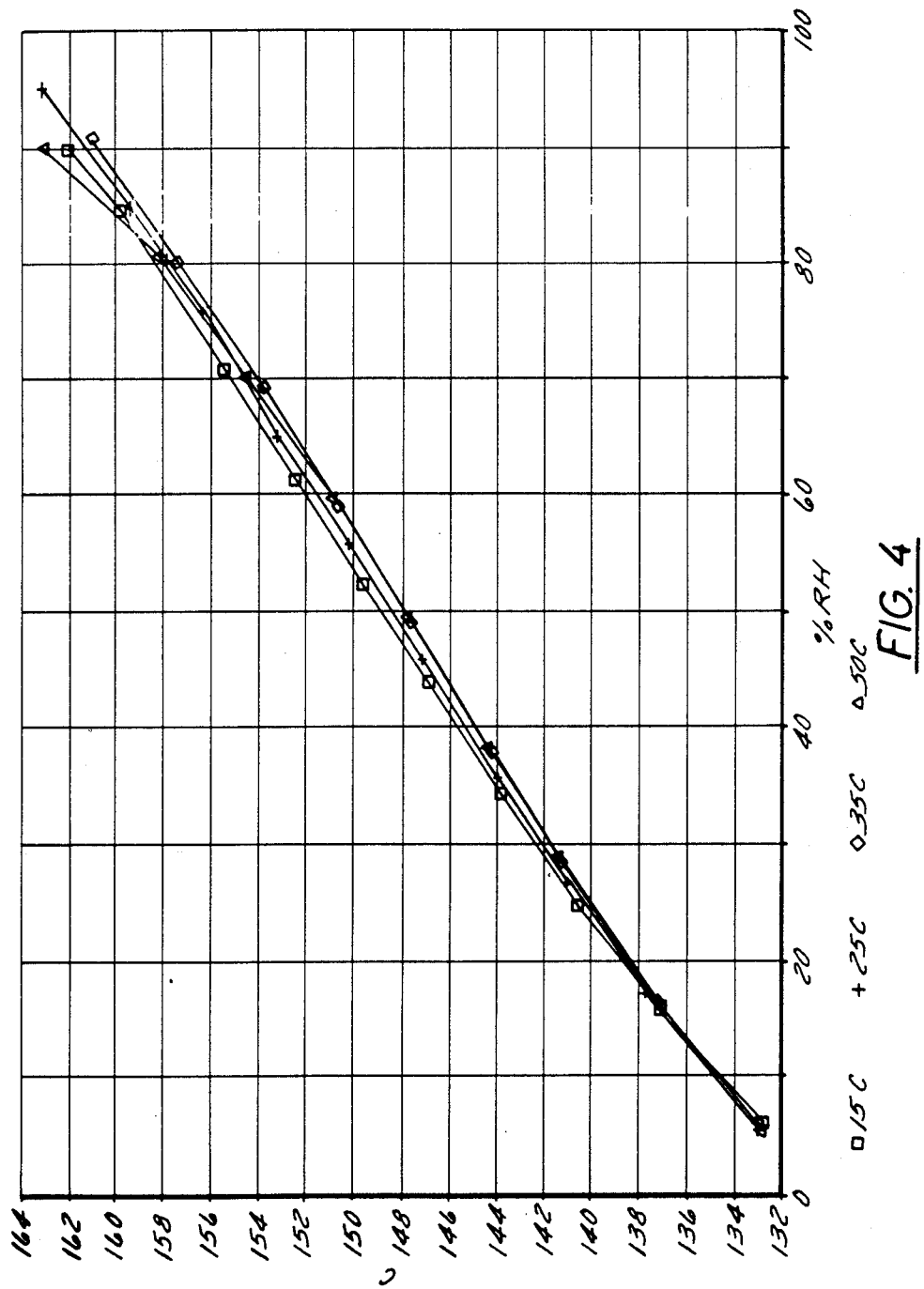
FIG. 4 is a graph plotting relative humidity versus capacitance in picofarads for a humidity sensor according to the invention at four different temperatures.

The following procedure was used to test the temperature sensing ability of the humidity sensor according to the invention of Example 1. The procedure used to determine the temperature sensing characteristics of the humidity sensor was the same as the procedure used to test the humidity sensing ability in Example 3. However, the procedure was repeated at four different temperatures: 15° C., 25° C., 35° C., and 50° C. A curve was plotted from the data at each of the four temperatures. Four curves which are very close to one another, as shown in FIG. 4, demonstrate that the polymeric capacitance humidity sensor of the invention was not particularly sensitive to changes in temperature, a highly valuable characteristic.

EXAMPLE 5

The following procedure was used to test the effect of chlorine on the humidity sensor of Example 1, as compared to a commercially available humidity sensor (gold on a polymeric film). Since the air around an indoor swimming pool contains chlorine, it is important that any humidity sensor used in this type of atmosphere be resistant to the corrosive effects of chlorine.

A sodium hypochlorite bleach solution containing 5% chlorine was placed in the bottom of a glass container, and the humidity sensors were suspended above the bleach solution. A glass cover was then replaced on the glass container to enclose the system. The relative humidity of the ambient room air was measured using the General Eastern Dew Point Hygrometer. Periodically, the humidity sensors were removed from the container and allowed to stabilize with the surrounding conditions for about 30 minutes. The capacitance of each humidity sensor was measured, and then the sensor was placed back in the enclosed glass container. These steps were repeated periodically for a period of about 700 hours.

Figure 5:
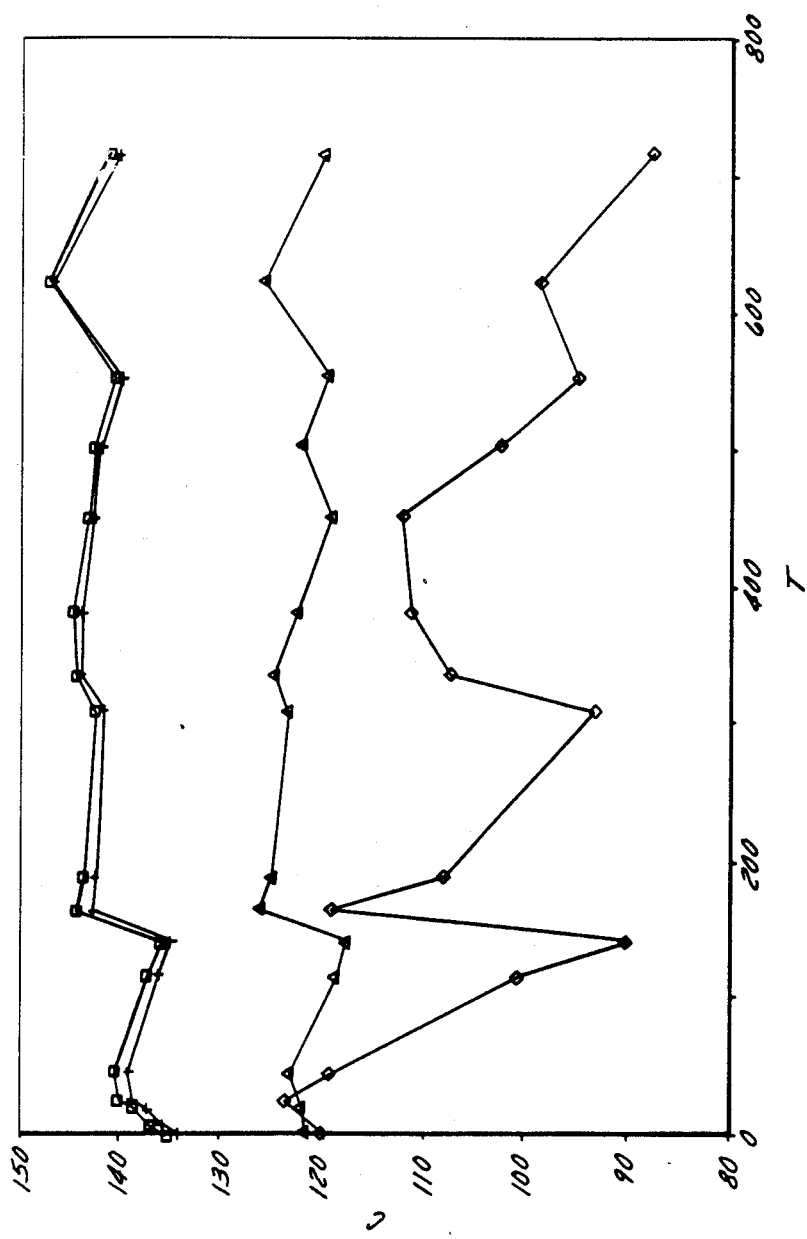
FIG. 5 is a graph plotting time versus capacitance in picofarads for a humidity sensor according to the invention and a comparative sensor under corrosive conditions, as described in Example 5 below.

In FIG. 5, the capacitance of the sensor according to the invention and the comparative humidity sensor are plotted versus time in hours. Boxes and crosses (the top two graphs) represent the invention. Triangles represent stated output for the comparative sensor (what it should have read.) Diamonds (bottom plot) represent the actual measured percentage relative humidity for the comparative sensor. As FIG. 5 shows, the sensor according to the invention showed remarkably low susceptibility to the corrosive effects of chlorine. The shape of the plot using the data from the sensor of the invention almost mirrors that of the plot using the expected results. By contrast, the plot using the reading generated by the comparative humidity sensor varies greatly from the plot of the expected data. This was evidence that the comparative humidity sensor was very vulnerable to the corrosive effects of chlorine.

We claim:

1. A humidity sensor element, comprising:
a thin, flexible film consisting essentially of a dielectric, water-absorbing first polymer having a dielectric constant which varies substantially linearly as a function of relative humidity, said first polymer comprising backbone chains containing heterocyclic units in which one or more atoms in the heterocyclic unit are nitrogen, and one or more carbon atoms in the heterocyclic unit have an oxygen atom double bonded thereto, said polymer being substantially free of hydroxyl groups, said first polymer having the general formula:

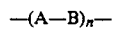

wherein A is a unit containing a heterocyclic unit including at least one —N—C═O linkage therein, B is an aromatic, alicyclic, or aliphatic, substituted or unsubstituted hydrocarbon unit, and n is at least about 10; and
a pair of thin, water-permeable, conductive layers disposed on opposite sides of said film and integrally bonded thereto, said conductive layers each consisting essentially of a second polymer having electrically conductive particles distributed therein, which conductive particles are effective to render said layers electrically conductive.

2. The element of claim 1, wherein said unit A contains at least one phthalimide ring structure, and unit B has the formula:

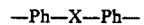

wherein Ph is a phenylene group and X is an oxygen atom or a lower alkylene group.

3. The element of claim 1, wherein said first polymer is a polyimide or poly(amide-imide).

4. The element of claim 3, wherein said second polymer is a poly(parabanic acid).

5. The element of claim 1, wherein said first polymer is a poly(iminoimidazolidinedione).

6. The element of claim 1, wherein said second polymer is the same as said first polymer.

7. The element of claim 6, wherein said conductive particles consist essentially of carbon particles.

8. The element of claim 7, wherein said carbon particles are chain forming.

9. The element of claim 7, wherein said conductive layers consist essentially of 10 to 80 wt. % of said carbon particles substantially uniformly distributed in 20 to 90 wt.% of said second polymer.

10. The element of claim 1, wherein said second polymer is a cellulosic polymer.

11. The element of claim 10, wherein said second polymer is cellulose acetate butyrate cross-linked with urea-formaldehyde or melamine-formaldehyde.

12. The element of claim 10, wherein said conductive particles consist essentially of carbon particles.

13. The element of claim 12, wherein said conductive layers consist essentially of 10 to 80 wt. % of said carbon particles substantially uniformly distributed in 20 to 90 wt.% of said second polymer.

14. The element of claim 12, wherein said carbon particles are chain-forming.

15. The element of claim 14, wherein the carbon particles have a particle size of about 10 microns or less.

16. The element of claim 10, wherein said cellulosic polymer is crosslinked.

17. The element of claim 1, wherein said second polymer has the general formula:

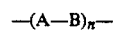

wherein A is a unit containing a heterocyclic unit including at least one —N—C═O linkage therein, B is an aromatic, alicyclic, or aliphatic, substituted or unsubstituted hydrocarbon unit, and n is at least about 10.

18. The element of claim 17 wherein said second polymer is a polyimide.

19. The element of claim 17 wherein said second polymer is a poly(parabanic acid).

20. The element of claim 1, wherein the film has a thickness of 0.01 inch or less.

21. The element of claim 20, wherein the conductive layers each have a thickness of 0.005 inch or less.

22. The element of claim 21, wherein the conductive layers have a resistivity of 500,000 ohm-cm or less, and the film has a resistivity of at least about $10^{13}$ ohm-cm at 35° C. and 50% relative humidity.

23. The element of claim 1, wherein the film has a thickness of 0.001 inch or less.

24. The element of claim 23 wherein the conductive layers each have a thickness of 0.0005 inch or less.

25. The element of claim 24, wherein the conductive layers have a resistivity of 125,000 ohm-cm or less, and the film has a resistivity of at least about $10^{15}$ ohm-cm at 35° C. and 50% relative humidity.

26. The element of claim 25, wherein the conductive particles consist essentially of chain-forming carbon particles having a particle size of about 1 micron or less.

27. The element of claim 1, wherein the first polymer consists essentially of units of the formula:

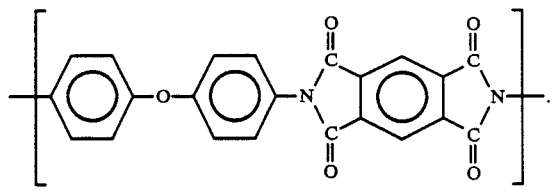

28. The element of claim 1, wherein the first polymer consists essentially of units of the formula:

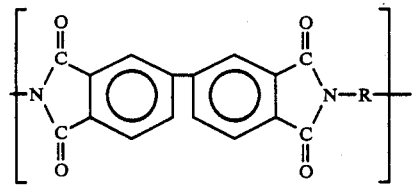

wherein R is aromatic, alicyclic or aliphatic.

29. The element of claim 1, wherein the first polymer consists essentially of units of the formula:

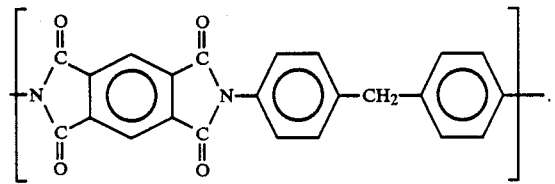

30. A humidity sensor element, comprising:
a thin, flexible film consisting essentially of a dielectric, water-absorbing first polymer made of poly(-parabanic acid) having a dielectric constant which varies substantially linearly as a function of relative humidity; and
a pair of water-permeable, conductive layers disposed on opposite sides of said film and integrally bonded thereto, said conductive layers each consisting essentially of a second polymer having electrically conductive particles distributed therein, which conductive particles are effective to render said layers electrically conductive.

31. The element of claim 30, wherein said second polymer is a cross-linked cellulosic polymer.

32. The element of claim 31, wherein said second polymer is cellulose acetate butyrate crosslinked with urea-formaldehyde or melamine-formaldehyde, and said conductive particles consist essentially of chain-forming carbon particles.

33. The element of claim 32, wherein said conductive layers consist essentially of 10 to 80 wt. % of said carbon particles substantially uniformly distributed in 20 to 90 wt.% of said second polymer.

34. The element of claim 30, wherein the poly(parabanic acid) consists essentially of units of the formula:

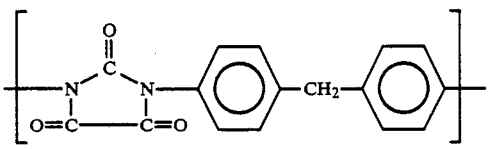

35. A humidity sensor element, comprising:
a flexible film having a thickness of 0.001 inch or less consisting essentially of a dielectric, water-absorbing polyimide made of units having the formula:

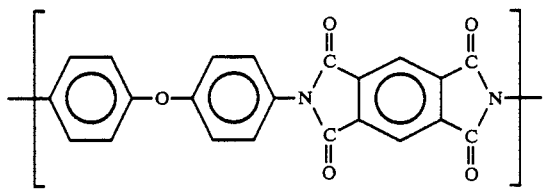

having a dielectric constant which varies substantially linearly as a function of relative humidity within the range of 5 to 95 percent relative humidity at temperatures in the range of 15 to 50° C., which film has a resistivity of at least about $10^{15}$ ohm-cm at 35° C. and 50% relative humidity;
a pair of water-permeable, conductive layers having a thickness of 0.0005 inch or less disposed on opposite sides of said film and integrally bonded thereto, said conductive layers each consisting essentially of about 20 to 90 wt. % of a cross-linked cellulosic polymer and about 10 to 80 wt. % of electrically conductive, chain-forming carbon particles having a particle size of about 1 micron or less, which particles are distributed in said cellulosic polymer so that said layer have a resistivity of 125,000 ohm-cm or less.

36. The element of claim 35, wherein said cellulosic polymer is cellulose acetate butyrate cross-linked with urea-formaldehyde.

37. A method for making a humidity sensor element, comprising:
(a) disposing a piece of a thin, flexible film made of a dielectric, water-absorbing first polymer having a dielectric constant which varies as a function of relative humidity on a holder of a screen printing apparatus;
(b) applying suction through the holder to the film to temporarily secure the film on the holder;
(c) positioning a stencil over the film;

(d) screen printing the film through the stencil with a liquid composition comprising an electrically nonconductive second polymer, electrically conductive particles and a carrier liquid;

(e) drying the liquid composition under conditions effective to form a water-permeable, first conductive layer on one side of said film and integrally bonded thereto, which conductive layer has a shape corresponding to the stencil;

(f) repeating steps (a)-(e) to form a second conductive layer on the face of the film opposite the first conductive layer.

38. The method of claim 37 wherein said first polymer has the general formula:

$$-(A-B)_n-$$

wherein A is a unit containing a heterocyclic unit including at least one $-N-C=O$ linkage therein, B is an aromatic, alicyclic, or aliphatic, substituted or unsubstituted hydrocarbon unit, and n is at least about 10.

39. The method of claim 38, wherein said first polymer is a polyimide.

40. The method of claim 38, wherein said first polymer is a poly(parabanic acid).

41. The method of claim 38, wherein the second polymer is a cross-linkable cellulosic polymer, and step (e) further comprises heating said film with said liquid composition printed thereon to cure said second polymer.

42. The method of claim 41, wherein the liquid composition comprises a mixture of said cross-linkable cellulosic polymer, chain-forming carbon particles, and an organic solvent.

43. The method of claim 42, wherein said cellulosic polymer is cellulose acetate butyrate with an amount of urea-formamaldehyde or melamine-formaldehyde effective for cross-linking therewith during step (e).

44. The method of claim 37, wherein the film has a thickness of 0.01 inch or less.

45. The method of claim 44 wherein the conductive layers each have a thickness of 0.005 inch or less.

46. The method of claim 37, wherein the film has a thickness of 0.001 inch or less.

47. The method of claim 46, wherein the conductive layers each have a thickness of 0.0005 inch or less.

* * * * *